United States Patent [19]

Clark et al.

[11] Patent Number: 5,736,492

[45] Date of Patent: Apr. 7, 1998

[54] ALKENYL-SUBSTITUTED DICARBOXYLIC DERIVATIVES

[75] Inventors: Michael Thomas Clark, Chester; Hendrik Tijmen Verkouw, Kent, both of Great Britain

[73] Assignee: Shell Oil Company, Houston, Tex.

[21] Appl. No.: 693,575

[22] Filed: Aug. 2, 1996

[30]     Foreign Application Priority Data

Sep. 8, 1995 [EP]  European Pat. Off. .............. 95306300

[51] Int. Cl.$^6$ ................................................. C10M 145/00
[52] U.S. Cl. ......................... 508/485; 508/486; 508/492; 560/190
[58] Field of Search .................................. 508/485, 486, 508/492; 560/190

[56]     References Cited

U.S. PATENT DOCUMENTS

| 3,522,179 | 7/1970 | Le Suer | 508/485 |
| 3,639,242 | 2/1972 | Le Suer | 508/485 |
| 5,273,672 | 12/1993 | Dasai et al. | 508/485 |

FOREIGN PATENT DOCUMENTS

| 490 454 | 6/1992 | European Pat. Off. . |
| 1483729 | 8/1974 | United Kingdom . |

OTHER PUBLICATIONS

S/Report dated Jun. 1, 1997.

*Primary Examiner*—Jacqueline V. Howard

[57]     ABSTRACT

The invention provides alkenyl-substituted dicarboxylic derivatives, having (a) an alkenyl group derived from an atactic propylene oligomer substantially of the formula

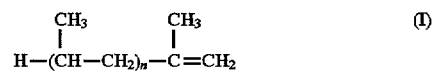

where n is in the range 15 to 120, having number average molecular weight ($M_n$) in the range 700 to 5000, and molar ratio dicarboxylic moieties to atactic propylene oligomer in the range 1:1 to 1.5:1; and having (b) an ester group derived from a polyol, which are useful as dispersant additives; a process for making the ester derivatives, additive concentrates containing such ester derivatives, and lubricating oil compositions.

18 Claims, No Drawings

ALKENYL-SUBSTITUTED DICARBOXYLIC DERIVATIVES

The present invention relates to alkenyl-substituted dicarboxylic acid or anhydride ester derivatives that are useful as dispersant additives in lubricating oil compositions, in the preparation of dispersant additives and to additive concentrates containing them.

BACKGROUND

UK patent No. 981,850 discloses the use of esters of polyisobutenylsuccinic acids which are obtained by reaction of polyisobutenylsuccinic acids with a polyhydric alcohol, e.g. pentaerythritol, as oil additives. The resulting products are known as dispersant additives for lubricating oils and are often referred to as "ashless" because of the absence of a metal component.

It has now been found that by using a particular class of polyolefins it is possible to prepare alkenyl ester dispersant additives for lubricating oils. These novel alkenyl ester dispersant additives display improved dispersancy properties when compared with the conventional esters described hereinabove.

SUMMARY OF INVENTION

According to the present invention there are provided alkenyl-substituted dicarboxylic acid ester derivatives and alkenyl-substituted dicarboxylic anhydride ester derivatives, having (a) an alkenyl group derived from an atactic propylene oligomer substantially of the formula:

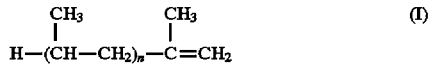

where n is in the range 15 to 120, having number average molecular weight ($M_n$) in the range 700 to 5000, and molar ratio of dicarboxylic acid ester derivatives or dicarboxylic anhydride moieties to atactic propylene oligomer is in the range of 1:1 to 1.5:1; and (b) an ester group derived from a polyol. The alkenyl-substituted dicarboxylic acid derivatives and the alkenyl-substituted dicarboxylic anhydride ester derivatives are useful as dispersant additives in lubricating oil composition and concentrates thereof.

DESCRIPTION OF THE INVENTION

The alkenyl-substituted dicarboxylic acid derivatives and the alkenyl-substituted dicarboxylic anhydride ester derivatives have (a) an alkenyl group derived from atactic propylene oligomer substantially of the formula

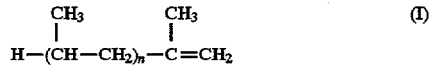

where n is in the range of 15 to 20, having an average molecular weight (Mn) in the range of 700 to 5000, and molar ratio of dicarboxylic acid or dicarboxylic anhydride moieties to atactic propylene oligomer is in the range of 1:1 to 1.5:1; and (b) an ester group derived from a polyol.

The atactic propylene may conveniently be prepared as described in EP-B-0 490,454 which is hereby fully incorporated by reference.

The number average molecular weight ($M_n$) of the atactic propylene oligomer is determined by quantitative reaction with ozone on the assumption that each oligomer chain contains one double bond, as will be readily understood by those skilled in the art.

An upper value ("maximum") of 5000 for $M_n$ of the atactic propylene oligomer is required due to the fact that molecular weights above 5000 can give handling problems in preparation of the alkenyl ester derivatives from the atactic propylene oligomer due to viscosity levels. A lower value ("minimum") of 700 for the $M_n$ is required because low molecular weight products tend to be less effective as dispersants.

Preferably, the alkenyl group is derived from an atactic propylene oligomer of formula I, which has n in the range 15 to 70 and $M_n$ in the range 700 to 3000, and more preferably n in the range 20 to 60 and $M_n$ is in the range 900 to 2500.

The polyol suitably comprises an alkane polyol such as without limitations, an alkylene diol or polyalkylene polyol.

Examples of appropriate alkane polyols, include without limitations, alkane polyols having at least two and preferably at least four hydroxy groups such as the trihydroxyalkanes, e.g. ethylene glycol, propylene glycol, polymethylene glycols, trihydroxybutanes, pentanes, hexanes, heptanes, octanes, nonanes, dodecanes, tetrahydroxy alkanes, pentahydroxy alkanes, hexahydroxy alkanes, and the sugar alcohols such as erythritol, pentaerythritol, tetritols, pentitols, hexitols, mannitol, sorbitol, sucrose, glucose and the like. The preferred polyols are glycerol and sorbitol.

In accordance with the invention, the alkenyl ester derivatives of the invention may be prepared by a process which comprises reacting an alkenyl-substituted dicarboxylic acid or anhydride with a polyol, both of which have been defined above.

The molar ratio of alkenyl-substituted dicarboxylic acid or alkenyl-substituted dicarboxylic anhydride to polyol used in the present process may vary between wide limits. A molar ratio of alkenyl-substituted dicarboxylic acid or anhydride to polyol is in the range 0.5 to 10, maybe used, preferably a molar ratio of 0.6 to 3. The reaction temperature may also vary between wide limits with reaction temperatures in the range 150° to 250° C. being preferred, the range 180° to 210° C. being more preferred. The reaction time may also vary with reaction times in the range 6 to 30 hours being preferred, with the range of 18 to 24 hours being more preferred.

A solvent may or may not be present in the reaction mixture. Examples of solvents include, without limitations, hydrocarbons, such as xylene, toluene and mineral oil; and ethers such as diphenylether; ketones; and chlorobenzene. Another embodiment of the invention an esterfication catalyst may be used in the reaction process.

Conventional esterfication catalysts may be used. Suitable esterification catalysts include mineral acids, sulphonic acids and $BF_3$, mineral acids being preferred.

Water vapor which is produced during the reaction can be removed from the reaction zone as the reaction proceeds, by application of methods well known in the art. Preferably, the reaction is carried out in a closed reaction vessel.

If the selected polyol is an alkane polyol, it may suitably be mixed with an amine, prior to reaction with one or more alkylene oxides.

Examples of amines, includes without limitation, aminoalcohols, polyoxyalkylene polyamines and hydroxyamines. Preferably, the amine is an amino-alcohol.

The molar ratio of dicarboxylic acid or dicarboxylic anhydride groups to polyol groups in the derivatives of the present invention is preferably in the range 0.5 to 10, with a range of 0.6 to 3 being more preferred.

The dicarboxylic acid maybe derived from an alpha-beta unsaturated dicarboxylic acid, anhydride or ester, such as maleic, fumaric, itaconic, Maleic acid and maleic anhydride are preferred, in which case the dicarboxylic acid grouping in the present product is thus a succinic acid derivative.

The alkenyl-substituted dicarboxylic acid is preferably derived by reacting an alpha-beta unsaturated dicarboxylic acid with the atactic propylene oligomer as described hereinabove.

The alkenyl-substituted dicarboxylic acid or anhydride may be prepared according to established procedures from atactic propylene oligomer as defined above of required molecular weight and an appropriate amount of the dicarboxylic acid or dicarboxylic anhydride. Thus, the atactic propylene oligomer may be contacted with, for instance, maleic acid or maleic anhydride ("MALA") at a temperature of 140° to 220° C., optionally in the presence of chlorine, e.g. as described in e.g. UK Patent 949,981 which is incorporated herein by reference. The proportions of atactic propylene oligomer and maleic anhydride and also chlorine, when used, are selected so as to yield the desired MALA/alkenyl group ratio in the final product. Another method for the preparation of polyolefin-substituted succinic anhydride is described in U.S. Pat. No. 3,172,892, incorporated herein by reference according to which a halogenated, which maybe chlorinated, alkenyl group is reacted with maleic anhydride.

From e.g. NL-A-74 12 057 it is known to prepare hydrocarbon-substituted succinic anhydride by thermally reacting an alkenyl group with maleic anhydride, a procedure which may be combined with that described in UK 949,981, as is illustrated in UK 1,440,219 and UK 1,543,627 which are incorporated herein by reference. The products prepared in this way include compounds in which the alkenyl chain is connected to the alpha and/or beta carbon atoms of the succinic group.

Preferably, the atactic propylene oligomer is reacted directly with maleic anhydride at a temperature in the range 175° C. to 250° C., preferably 190° C. to 235° C., more preferably 200° C. to 235° C. The molar ratio of maleic anhydride to atactic propylene oligomer is advantageously in the range 1:1 to 5:1, preferably 1.2:1 to 4:1, more preferably 1.5:1 to 3.6:1.

The molar ratio dicarboxylic acid or dicarboxylic anhydride moieties to atactic propylene oligomer (r) of the alkenyl-substituted dicarboxylic acid or alkenyl-substituted dicarboxylic anhydride is readily calculated from the expression:

$$r = \frac{M_n \times AV}{(20 \times AM - AV \times 96)}$$

in which:
$M_n$=Number average molecular weight of the atactic propylene oligomer
AV=Acid value of the reaction product (mmol/g)
AM="Active matter" in the reaction product (%m)
"Active matter" denotes propylene oligomer bearing carboxylic acid groupings, from which it will be understood that the unreacted nonpolar polyolefins do not contribute to the AM.

Preferably, the molar ratio dicarboxylic acid or anhydride acid moieties to atactic propylene oligomer is in the range of 1:1 to 1.3:1, more preferably 1:1 to 1.2:1.

It is preferred that at least 90% by weight (w), preferably at least 95%w, of the atactic propylene oligomer is of formula I.

Number average molecular weight ($M_n$) and weight average molecular weight ($M_w$) can be determined by gel permeation chromatography, with suitable calibration, in order to determine the ratio $M_w/M_n$, which is a measure indicating the width of molecular weight distribution. $M_w/M_n$ values for polyolefins typically fall in the range 1.5 to 4.0. For the atactic propylene oligomers from which the ester derivatives of the present invention are prepared, $M_w/M_n$ determined by gel permeation chromatography is preferably 2.5 or less, more preferably 2 or less.

The alkenyl-substituted dicarboxylic acid ester derivatives or alkenyl-substituted dicarboxylic anhydride ester derivatives of the present invention are useful as additives for lubricating oil compositions and hydrocarbon fuels such as gasolines.

Accordingly, the present invention further provides a lubricating oil compositions which comprise a major proportion (more than 50%w) of lubricating oil and a minor proportion, preferably from 0.1 to 10%w, especially 0.5 to 5%w, based on the total composition, of an alkenyl-substituted dicarboxylic acid or alkenyl-substituted dicarboxylic anhydride derivatives.

The lubricating oil compositions may also comprise a mixture of an alkenyl-substituted dicarboxylic acid ester derivatives or alkenyl-substituted dicarboxylic anhydride ester derivatives containing different polyether polyol groups.

The lubricating oil used in such compositions may be natural, mineral or synthetic in origin. Natural lubricating oils include animal and vegetable oils, such as castor oil. Mineral oils comprise the lubricating oil fractions derived from crude oils, coal or shale, which fractions may have been subjected to certain treatments such as clay-acid, solvent or hydrogenation treatments. Synthetic lubricating oils include synthetic polymers of hydrocarbons, modified alkylene oxide polymers, and ester lubricants, which are known in the art. These lubricating oils are preferably crankcase lubricating oils for spark-ignition and compression-ignition engines, but also include hydraulic lubricants, metal-working fluids and automatic transmission fluids. Preferably the lubricating base oil component of the compositions according to the present invention is a mineral lubricating oils or a mixture of mineral lubricating oils such as those sold by member companies of the Royal Dutch/Shell Group under the designations "HVI", or "XHVI" (trademark).

The lubricating oil compositions of the present invention may also contain various other additives, such as viscosity index improvers ("VI"). Suitable VI improvers include, without limitation, linear or star-shaped polymers of a diene such as isoprene or butadiene, or a copolymer of such a diene with optionally substituted styrene. The copolymers are suitably block copolymers and are preferably hydrogenated to such an extent as to saturate most of the olefinic unsaturation. Other suitable additives include dispersant V.I. improvers such as those based on block copolymers, or polymethacrylates, extreme pressure/anti-wear additives (such as zinc or sodium dithiophosphates), anti-oxidants, friction modifiers or metal-containing detergents such as phenates, sulphonates, alkylsalicylates or naphthenates, all of which detergents may be overbased.

The lubricating oil compositions according to the present invention have excellent dispersancy properties.

The lubricating oil compositions according to the present invention are suitably prepared by blending an additives concentrate into the lubricating base oil. Such concentrate generally comprises a lubricating oil as solvent/diluent and one or more additives in a concentrated form. Accordingly, the present invention further provides lubricating oil concentrates that comprise lubricating oil and a polyolefin-substituted dicarboxylic acid or polyolefin-substituted dicarboxylic anhydride derivative as described hereinabove. The derivative is present in an amount of 10 to 80%w based on the total concentrate.

The present invention will be further illustrated by the following Examples which are included for illustrative purposes only and are not to be construed as limiting the invention.

Active matter content was determined by separating inactive material from the desired active matter on an aluminium oxide column using diethyl ether as eluant (AMS 807). Acid value was determined by potentiometric titration with aqueous potassium hydroxide of a weight amount of product dissolved in a toluene/methyl ethyl ketone/t-butanol/water mixture (SMS 2746).

EXAMPLE 1

An atactic propylene oligomer (APO) (Mn 835) was prepared by a method analogous to that disclosed in Examples 1 to 4 of EP-B-0490454. The atactic propylene oligomer (21.37 kg, 25.23 mol) and maleic anhydride (MALA) (4.63 kg, 47.24 mol) were heated together at reflux temperature (225° C.) in a glass reactor equipped with baffles, turbine stirrer, reflux condenser, nitrogen inlet, temperature probe and electrical heating mantle for 4 hours. Unreacted MALA was removed by vacuum distillation. The residue was then allowed to cool to ambient temperature (20° C.), diluted with heptane to about 50% w and insoluble matter was removed by filtration. The heptane was then evaporated off yielding a clear, light yellow viscous liquid product (25.0 kg) which was found to have active matter content of 77.9 %w and acid value 1.87 milli-equivalents/g (meq/g). This analysis data indicates a succination ratio of 1.14 mol MALA/ mol propylene oligomer. Results are given in Table 1.

EXAMPLE 2

A mixture of 2.5 kg (2.66 mol) polyisobutylene (PIB) (Mn 950) and 391 g (3.99 mol) of maleic anhydride (MALA), yielding a molar ratio of maleic anhydride to polyisobutylene of 1.5, was heated to 235° C. over 4 hours. The excess maleic anhydride was removed by evaporation under reduced pressure yielding a product which was found to have active matter content of 67.8 %w and acid value 1.52 milli-equivalents/g (meq/g). This analysis data indicates a succination ratio of 1.2 mol MALA/ mol polyisobutylene. Results are given in Table 1.

EXAMPLE 3

The APO-MALA product (51.55 g, 0.062 mol) obtained in Example 1, 47 g of a HVI 60 oil and pentaerythritol (PENTA) (10.94 g, 0.08 mol) were heated at 200° C. for 12 hours in an autoclave. The product so obtained was a clear dispersant which was found to have active matter content of 50.0 %w and acid value 0.08 milli-equivalents/g (meq/g). This analysis data indicates an esterification ratio of 1:1.3 mol APO-MALA/mol PENTA. Results are given in Table 1.

EXAMPLE 4

The PIB-MALA product (121.0 g, 0.066 mol) obtained in Example 2 was subjected to a similar process as described in Example 3, except that 11.75 g (0.086 mol) PENTA was used. The resultant reaction mixture was then heated at 200° C. for 12 hours in an autoclave. The product obtained was a clear dispersant which was found to have active matter content of 67.2 %w and acid value 0.08 milli-equivalents/g (meq/g). This analysis data indicates an esterification ratio of 1:1.3 mol PIB-MALA/ mol PENTA. Results are given in Table 1.

EXAMPLE 5

The APO-MALA product (70.0 g, 0.65 mol) obtained in Example 1 was reacted at 160° C. with tri-ethylene tetramine (TETA) (56.7 g, 0.36 mol) at an APO-MALA to amine ratio of 1:0.55 for about 4 hours. The reaction mixture was then filtered to yield the desired product, which was found to have active matter content of 78.7 %w and acid value 0.02 meq/g. Results are given in Table 1 and 2.

EXAMPLE 6

The products of Examples 3 to 5 and a commercially available PIB-MALA-TETA composition were each diluted to an active matter content of 50%w by addition of "HVI 60" base oil (a bright and clear high viscosity index base oil having viscosity at 100° C. 4.4 to 4.9 mm$^2$/s (ASTM D 2270)). The resulting concentrates were then tested as follows:

Carbon Black Dispersancy Test (CBDT) (British Rail publication BR 669: 1984)

Samples of a SAE 15W40 Middle East lubricating oil containing a commercial package of a zinc dialkyldithiophosphate, an overbased calcium alkyl salicylate and VI improver, were modified by incorporation of concentrate to give oils containing the products of Examples 3 to 5 and the commercially available PIB-MALA-TEPA composition at a concentration of 1%w active matter. 3%w of carbon black was then added to each oil and (percentage) increase in kinematic viscosity at 60° C. was determined using an Ubbelohde viscometer. A low result is an indication of less sludge forming in engines and indicates therefore good dispersant performance.

The results are shown in Table 2. It will be clear from Table 2 that the composition according to the present invention (Example 3) performs much more attractively than conventional compositions falling just outside the scope of the present invention (Examples 4 to 5, and the commercially available PIB-MALA-TEPA composition).

TABLE 1

| Product of Ex. | Product | | |
|---|---|---|---|
| | Active matter (% w) | Acid value (meg/g) | Succ/ester. Ratio |
| 1 | 77.9 | 1.67 | 1.14 |
| 2 | 67.8 | 1.52 | 1.20 |
| 3 | 50.0 | 0.08 | 1.3 |
| 4 | 67.2 | 0.08 | 1.3 |
| 5 | 78.7 | 0.02 | — |

TABLE 2

| Product of Example | CBDT (%) |
|---|---|
| 3 | 32.0 |
| 4 | 37.0 |
| 5 | 45.1 |
| * | 46.3 |

*Commercially available PIB-MALA-TETA composition

We claim:

1. An alkenyl-substituted dicarboxylic acid ester derivative having (a) an alkenyl group derived from an atactic propylene oligomer substantially of the formula:

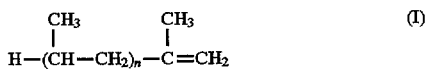

where n is in the range 15 to 120, having number average molecular weight ($M_n$) in the range 700 to 5000, and molar ratio dicarboxylic acid to atactic propylene oligomer in the range 1:1 to 1.5:1; and (b) having an ester group derived from a polyol.

2. An ester derivative according to claim 1, wherein the alkenyl group is derived from an atactic propylene oligomer of formula I which has n in the range 15 to 70 and $M_n$ in the range 700 to 3000.

3. An ester derivative according to claim 2, wherein n is in the range 20 to 60 and $M_n$ is in the range 900 to 2500.

4. An ester derivative according to any one of claim 1, wherein the molar ratio dicarboxylic acid to atactic propylene oligomer is in the range 1:1 to 1.3:1.

5. An ester derivative according to claim 4, wherein the molar ratio is in the range 1:1 to 1.2:1.

6. An ester derivative according to claim 5, wherein the polyol is an alkane polyol having at least two hydroxy groups.

7. An ester derivative according to claim 6, wherein the alkane polyol is pentaerythritol, glycerol, sorbitol, sucrose or combinations thereof.

8. An ester derivative according to claim 7, wherein the molar ratio dicarboxylic acid groups to polyol groups is in the range 0.5 to 10.

9. An ester derivative according to claim 8, wherein the molar ratio of dicarboxylic acid groups to polyol groups is in the range of 0.6 to 3.

10. An ester derivative according to claim 9, wherein at least 95% weight (w) of the atactic propylene oligomer is of formula I.

11. An ester derivative according to claim 10, wherein the value $M_w/M_n$ of the atactic propylene oligomer as determined by gel permeation chromatography, is 2.5 or less.

12. A process for preparing an ester derivative according to claim 1 which comprises reacting an alkenyl-substituted dicarboxylic acid having an alkenyl group derived from an atactic propylene oligomer of the formula:

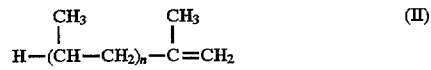

where n is in the range of 15 to 120, having a number average molecular weight ($M_n$) in the range of 700 to 5000, and molar ratio dicarboxylic acid moieties to atactic propylene oligomer in the range of 1:1 to 1.5:1, with a polyol.

13. A process according to claim 12, wherein the process occurs at temperature in the range 150° C. to 250° C.

14. A process according to claim 13, wherein the molar ratio alkenyl-substituted dicarboxylic acid to polyol is in the range of 0.5 to 10.

15. A lubricating oil composition which comprises a major proportion of a lubricating oil and a minor proportion of an ester derivative which is obtained by reacting an alkenyl-substituted dicarboxylic acid having an alkenyl group derived from an atactic propylene oligomer of the formula:

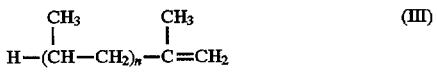

where n is in the range of 15 to 120, having a number average molecular weight (Mn) in the range of 700 to 5000 and a molar ratio of dicarboxylic acid moieties to atactic propylene oligomer in the range 1:1 to 1.5:1, with a polyol.

16. A lubricating oil composition according to claim 15, which contains from 0.1 to 10%w, based on the total composition, of an ester derivative.

17. A lubricating oil concentrate which comprises a lubricating oil and 10 to 80%w, based on the total concentrate, of an ester derivative according to claim 1.

18. An alkenyl-substituted dicarboxylic anhydride ester derivative having (a) an alkenyl group derived from atactic propylene oligomer substantially of the formula:

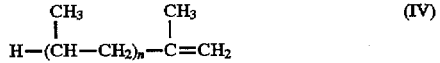

where n is in the range 15 to 120, having number average molecular weight ($M_n$) in the range 700 to 5000, and molar ratio dicarboxylic acid to atactic propylene oligomer in the range 1:1 to 1.5:1; and (b) having an ester group derived from a polyol.

* * * * *